United States Patent [19]

Marfat

[11] Patent Number: 5,217,968
[45] Date of Patent: Jun. 8, 1993

[54] N-ALKENYLBENZO(B)THIENO (3,2-B)OXAZIN-2,4-DIONES

[75] Inventor: Anthony Marfat, Mystic, Conn.

[73] Assignee: Pfizer Inc., New York, N.Y.

[21] Appl. No.: 761,735

[22] PCT Filed: Apr. 6, 1989

[86] PCT No.: PCT/US89/01424
§ 371 Date: Sep. 13, 1991
§ 102(e) Date: Sep. 13, 1991

[51] Int. Cl.$^5$ .................. C07D 413/00; A61K 31/535
[52] U.S. Cl. .................................. 514/229.8; 544/95; 544/96
[58] Field of Search .................. 544/96, 95; 514/229.8

[56] References Cited
U.S. PATENT DOCUMENTS
3,925,386 12/1975 Jager et al. .
4,656,265 4/1987 Lombardino et al. .
4,760,086 7/1988 Tischler et al. .

FOREIGN PATENT DOCUMENTS
0160408 11/1985 European Pat. Off. .
2132763 1/1973 Fed. Rep. of Germany .
2160523 12/1985 United Kingdom .
2193961 2/1988 United Kingdom .

OTHER PUBLICATIONS
Chem. Abst. vol. 106 No. 13 p. 42 95809q (1987).

Primary Examiner—Mukund J. Shah
Assistant Examiner—Matthew V. Grumbling
Attorney, Agent, or Firm—Peter C. Richardson; Paul H. Ginsburg; Valerie M. Fedowich

[57] ABSTRACT

N-Alkenylbenzo[b]thieno[3,2-b]oxazin-2,4-diones, pro-drugs of cyclooxygenase and 5-lipoxygenase inhibitory N-alkenyl-3-hydroxybenzo[b]thiophene-2-carboxamide derivatives; pharmaceutical compositions comprising one or more of said pro-drugs and a pharmaceutical acceptable carrier; and the use of said pro-drugs to treat mammalian diseases arising from biological mediators formed in the mammalian body by cyclooxygenase and/or 5-lipoxygenase catalyzed reactions.

12 Claims, No Drawings

N-ALKENYLBENZO(B)THIENO (3,2-B)OXAZIN-2,4-DIONES

BACKGROUND OF THE INVENTION

This invention relates to pro-drugs of certain 3-hydroxybenzothiophenes which have a 2-enamido side chain. More particularly it relates to cyclic pro-drugs of N-alkenyl-3-hydroxybenzo[b]thiophene-3-carboxamides which exhibit cyclooxygenase and 5-lipoxygenase inhibitory action, pharmaceutical compositions thereof, and the use thereof to treat various mammalian diseases.

U.S. Pat. No. 4,760,086, issued Jul. 26, 1988, describes a large number of N-alkenyl-3-hydroxybenzo[b]-thiophene-3-carboxamides of formula (I)

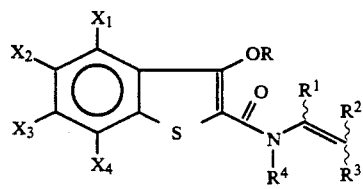

wherein each of $X_1$-$X_4$, R and $R^1$-$R^4$ are broadly defined as lower alkyl, aryl, heteroaryl, lower cycloalkyl, benzyl, lower alkenyl or lower alkynyl any of which may be substituted by a variety of substituents.

Said compounds are disclosed to be effective inhibitors of cyclooxygenase and 5-lipoxygenase and, therefore, of value in the treatment of inflammation, pain, fever and other prostaglandin and/or leukatriene mediated diseases.

U.S. Pat. No. 4,656,265, issued Apr. 7, 1987, describes cyclic pro-drugs of non-steroidal anti-inflammatory oxicams. In said pro-drugs, the parent oxicams are chemically modified to form a fused 1,3-oxazine ring system, which, in vivo, is cleaved to restore the parent compound.

SUMMARY OF THE INVENTION

This invention provides compounds of formula (II) below

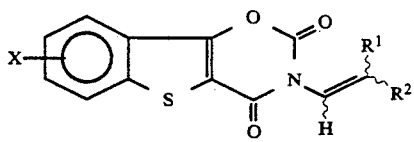

wherein X is hydrogen, trifluoromethyl, fluoro, chloro, lower alkyl, lower alkoxy, lower alkylthio, phenyl or 2,4-difluorophenyl;

each of $R^1$ and $R^2$ is hydrogen, phenyl, substituted phenyl wherein the substituent is chloro, fluoro, lower alkyl, lower alkoxy, lower alkylthio or hydroxy; furyl, thienyl, substituted thienyl wherein the substituent is lower alkyl, chloro or fluoro; lower alkyl, chloro, lower alkoxycarbonyl; furyl or pyrryl, which compounds are cyclic pro-drugs of compounds of formula (I) above wherein each of R, $R^1$ and $R^4$ is hydrogen.

The substituents ($R^1$ and $R^2$) on the double bond can be syn, anti or a mixture of both. Thus, in formula (II), substituents $R^1$ and $R^2$ are indicated as being attached to the double bond by wavy lines. This representation is intended to depict all forms of the isomers of formula (II) compounds. The individual isomers of formula (II) compounds can be prepared by starting with the appropriate isomer of the requisite formula (I) reactant. Alternatively, the isomers can be separated from a mixture thereof by known methods such as chromatography.

Formula (II) compounds, unlike the parent compounds of formula (I), are not enolic acids and, therefore, show less gastric irritation than do the parent compounds. Following their administration to a mammal, including a human, formula (II) compounds release the parent compound by some metabolic process.

Also included in this invention are pharmaceutical compositions suitable for administration to a mammal, including a human, said compositions comprising a pharmaceutically acceptable carrier and a cyclooxygenase and/or 5-lipoxygenase inhibiting amount of a compound of formula (II); and a method of treating diseases arising from biological mediators formed by cyclooxygenase and/or 5-lipoxygenase catalyzed reactions in a mammalian body which comprises administering to a mammal in need of such treatment a cyclooxygenase and/or 5-lipoxygenase inhibiting amount of a compound of formula (II).

DETAILED DESCRIPTION OF THE INVENTION

Compounds of formula (II) are prepared by reacting a compound of formula (I) wherein each of R, $R^1$ and $R^4$ is hydrogen with phosgene as cyclizing agent in a reaction-inert solvent in the presence of an acid binding agent at a temperature of $-70°$ C. to $+50°$ C.

Suitable reaction-inert solvents, i.e., solvents which do not react with reactants or products in such a manner as to reduce yield of the desired product, are halogenated hydrocarbons such as methylene chloride, chloroform, carbon tetrachloride and 1,2-dichloroethane; ethers such as ethyl or isopropyl ether, dioxane and tetrahydrofuran; acyclic hydrocarbons such as pentane, hexane and heptane; aromatic hydrocarbons such as benzene, toluene and xylene; cyclic hydrocarbons such as cyclopentane and cyclohexane; ethyl acetate, dimethylformamide, acetonitrile and dimethylsulfoxide. Preferred solvents are methylene chloride, ethyl ether, tetrahydrofuran and ethyl acetate.

Cyclizing agents other than phosgene can, of course, be used. Representative of such agents are those of the formula Y-COCl where Y is $(C_{1-4})$alkoxy, phenoxy, benzyloxy or trichloromethoxy. Phosgene is, however, the preferred cyclizing agent.

Suitable acid binding agents for use in the invention process are those basic compounds which will bind the hydrogen chloride formed in the reaction but will not form an unwanted by-product with the reagent Y-COCl or compounds of formula (I) under the conditions employed. Examples of suitable acid binding agents include tertiary amines such as the trialkylamines having from 3 to 30 carbon atoms, dialkyl aryl amines and alkyl diaryl amines having 8 to 30 carbon atoms, aralkyl dialkyl amines having from 9 to 30 carbon atoms, N-alkyl heterocyclic amines having from 6 to 25 carbon atoms; alkali metal or alkaline earth carbonates or bicarbonates, and alkaline earth oxides or hydroxides. Particularly preferred acid binding agents are sodium bicarbonate, calcium carbonate, calcium oxide, N,N-dimethylaniline, N-methylmorpholine and N-methylpiperidine. Most particularly preferred is triethylamine.

In theory the cyclizing agent, Y-COCl, and the starting compound of formula (I) are required in equimolar amounts to form the desired, respective products of formula (II). In practice, however, an excess of the cyclizing agent is ordinarily employed in order to ensure completion of reaction and to minimize the formation of unwanted by-products. Typically, a molar excess of from about 1 to 10 times is employed with good results.

The reaction can be conducted over a temperature range of from about −70° C. to +50° C. The favored temperature range is from −30° C. to 30° C. The preferred temperature range is from −10° C. to 25° C. with 0° C. to 25° C. being the especially preferred range.

The reaction is generally complete in less than four hours and the products isolated and purified by standard methods known to those skilled in the art.

The starting materials of formula (I) are available by procedures described in U.S. Pat. No. 4,706,086. The cyclizing agents are commercially available as are the acid-binding agents.

The cyclic prodrugs of this invention are evaluated for their anti-inflammatory activity according to known methods by administering multiple oral doses in model tests such as the rat foot edema test, rat adjuvant-induced arthritis test or phenylbenzoquinone-induced writhing test in mice, as described in U.S. Pat. No. 4,760,086 and elsewhere in the literature; see e.g., C. A. Winter, in "Progress in Drug Research" edited by E. Jucker, Birkhauser Verlag, Basel, Vol. 10, 1966, pp. 139-192.

In comparison with the parent compounds of formula (I), the novel pro-drugs of formula (II) are found to have markedly reduced ability to inhibit prostaglandin synthesis from arachidonic acid in tests carried out by a modification of the method of T. J. Carty et al., *Prostaglandins*, 19, 51-59 (1980). In the modified procedure cultures of rat basophilic leukemic cells (RBL-1), prepared by the method of Jakschik et al., ibid, 16, 733 (1978), are employed in place of mouse fibroblast (MC5-5) and rabbit synovial cell cultures. Thus, the invention compounds themselves are relatively inactive as anti-inflammatory agents, but they give rise to an active anti-inflammatory compound upon hydrolysis in vivo. Since the compound (II) is not an enolic acid and it is known that the hydrolysis takes place after the pro-drug leaves the stomach, they will significantly reduce the gastric irritation caused by oral administration of the parent enolic oxicams.

On a molar basis, the present pro-drugs are generally dosed at the same level and frequency as the parent from which they are derived. However, the non-enolic nature of the present compounds will generally permit higher tolerated doses, when such higher dosage is required in the control of inflammation.

In general, the invention compounds are administered via either the oral, parenteral or topical routes in doses ranging from about 0.01 mg to 150 mg per kg of body weight, although variations will necessarily occur depending upon the weight and condition of the subject being treated and the particular route of administration chosen. However, a dosage level that is in the range of from about 0.5 mg to about 7.5 g per patient per day is most desirably employed. Nevertheless, variations may occur depending upon the species of animal being treated and its individual response to said medicament, as well as on the type of pharmaceutical formulation and the time period and interval at which such administration is carried out. In some instances, dosage level below the lower limit of the aforesaid range may be more than adequate, while in other cases still larger doses may be employed without harmful side effects provided that such higher dose levels are first divided into several smaller doses for administration throughout the day.

The present pro-drugs are also formulated in the same manner and administered by the same routes as the parent compounds as described in U.S. Pat. No. 4,760,086. The preferred route of administration is oral, thus taking particular advantage of the nonenolic nature of the present compounds.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium sterate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes, and, if so desired, emulsifying and/or suspending agents as well, together with such diluents as water, ethanol, propylene glycol, glycerin and various like combinations thereof.

For purposes of parenteral administration, solutions in either sesame or peanut oil or in aqueous propylene glycol may be employed, as well as sterile aqueous solutions of the corresponding water-soluble alkali metal or alkaline-earth metal salts previously enumerated. Such aqueous solutions should be suitably buffered, if necessary, and the liquid diluent first rendered isotonic with sufficient saline or glucose. These particular solutions are especially suitable for intravenous, intramuscular and subcutaneous injection purposes. Additionally, it is also possible to administer the aforesaid compounds topically and this may be preferably done by way of creams, salves, jellies, pastes, ointments and the like, in accordance with standard pharmaceutical practice.

This invention is still further illustrated by the following examples, which are not to be construed as imposing limitations upon the scope thereof. On the contrary, it is to be clearly understood that resort may be had to various other embodiments, modifications and equivalents thereof which readily suggest themselves to those skilled in the art without departing from the spirit of the present invention and/or the scope of the appended claims.

EXAMPLE 1

N-[2-phenyl-2-(2-thienyl)ethenyl]-3-hydroxy-5-trifluoromethyl-benzo[b]thieno[3,2-b]oxazin-2,4-dione 3-Hydroxy-5-trifluoromethyl-N-[2-(2-thienyl)-2-phenylethenyl]benzo[b]thiophene-2-carboxamide (0.2 g, 0.448 mmole) was dissolved in 30 ml of dry methylene chloride and cooled to 0° C. under nitrogen. Triethylamine (0.156 ml, 1.12 mmole) was added and the reaction mixture stirred at 0° C. for several minutes. This was followed by bubbling in excess of phosgene gas. The reaction mixture was then stirred at 0° C. for about 1 hour followed by warming to room temperature at which point TLC analysis [CH$_2$Cl$_2$/hexane (2:1)]showed nearly complete consumption of starting material and formation of a single more polar product. The reaction was stirred at room temperature for an additional 2 hours followed by gentle warming to remove excess phosgene. The reaction mixture was diluted with ethyl acetate (200 ml) and washed with 2N HCl (2×100 ml), water (1×100 ml), brine and dried (Na$_2$SO$_4$). Concentration of the ethyl acetate extract in vacuo gave a total of 210 mg of dark yellow-brown oil which was purified on a silica gel column (CH$_2$Cl$_2$), affording 0.17 g of light brown foamy solid. Recrystallization from toluene-hexane gave an orange-brown crystalline solid, m.p. 208°–210° C., comprising a mixture of isomers: high resolution mass spectra M$^+$=471.0225 calcd. for C$_{23}$H$_{12}$O$_3$NS$_2$F$_3$ 471.0212. IR GKBr 1700 and 1780 cm$^{-1}$.

EXAMPLE 2

Isomeric Forms of the Example 1 Product

The procedure of Example 1 was repeated but using as reactants the individual isomers, identified as isomers A and B, of the Example 1 starting material. The isomer A product melted at 180°–182° C.; the isomer B product at 219°–221° C.

EXAMPLE 3

In like manner, following the procedure of Example 1 mutis mutandi, the compounds listed below are prepared.

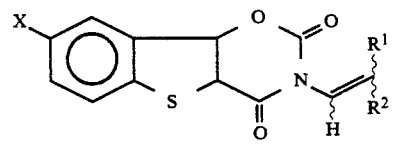

| X | R$^1$ | R$^2$ |
|---|---|---|
| H | CH$_3$ | CH$_3$ |
| H | 2-thienyl | phenyl |
| 5-CF$_3$ | 2-thienyl | 2-thienyl |
| 5-CF$_3$ | 2-(5-CH$_3$thienyl) | phenyl |
| 5-CF$_3$ | C$_6$H$_5$ | C$_6$H$_5$ |
| 4-CF$_3$ | C$_6$H$_5$ | C$_6$H$_5$ |
| 5-F | C$_6$H$_5$ | C$_6$H$_5$ |
| 5-CH$_3$ | C$_6$H$_5$ | 4-CH$_3$phenyl |
| 5-CH$_3$ | C$_6$H$_5$ | C$_6$H$_5$ |
| 5-CH$_3$ | 3-Fphenyl | 3-Fphenyl |
| 4-CH$_3$O | phenyl | phenyl |
| 5-Cl | phenyl | phenyl |
| 5-CF$_3$ | 4-CH$_3$Ophenyl | phenyl |
| 5-(2,4-F$_2$C$_6$H$_3$) | phenyl | phenyl |
| 5-CH$_3$S | 2-thienyl | phenyl |
| 5-CF$_3$ | 4-CH$_3$Ophenyl | 4-CH$_3$Sphenyl |
| 6-CF$_3$ | phenyl | pyrryl |
| 7-CF$_3$ | 4-CH$_3$Sphenyl | 2-furyl |
| 5-CF$_3$ | 4-HOphenyl | 4-CH$_3$Sphenyl |
| 5-CF$_3$ | 4-CH$_3$phenyl | 4-CH$_3$phenyl |
| 5-phenyl | phenyl | phenyl |
| 5-CF$_3$ | 4-OHphenyl | 4-OHphenyl |

I claim:
1. A compound of the formula (II)

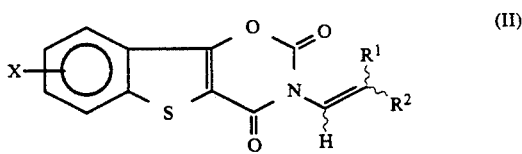

wherein X is hydrogen, trifluoromethyl, fluoro, chloro, lower alkyl, lower alkoxy, lower alkylthio, phenyl or 2,4-difluorophenyl;

each of R$^1$ and R$^2$ is hydrogen, phenyl, substituted phenyl wherein the substituent is chloro, fluoro, lower alkyl, lower alkoxy, lower alkylthio or hydroxy; furyl, thienyl, substituted thienyl wherein the substituent is lower alkyl, chloro or fluoro; lower alkyl, chloro, lower alkoxycarbonyl; furyl or pyrryl.

2. A compound according to claim 1, said compound having the formula wherein each of X, R$^1$ and R$^2$ are as defined in claim 1.

3. A compound according to claim 2 wherein X is hydrogen, lower alkyl or trifluoromethyl; each of R$^1$ and R$^2$ is lower alkyl, phenyl, substituted phenyl wherein the substituent is chloro, fluoro, hydroxy, lower alkyl or lower alkoxy; thienyl; methyl thienyl; furyl or pyrryl.

4. A compound according to claim 3 wherein X is hydrogen.

5. The compound according to claim 4 wherein X is hydrogen and each of R$^1$ and R$^2$ is phenyl.

6. The compound according to claim 4 wherein X is hydrogen; R$^1$ is phenyl and R$^2$ is 2-thienyl.

7. A compound according to claim 3 wherein X is trifluoromethyl.

8. The compound according to claim 7 wherein X is trifluoromethyl; and each of R$^1$ and R$^2$ is phenyl.

9. The compound according to claim 7 wherein X is trifluoromethyl; R$^1$ is phenyl and R$^2$ is 2-thienyl.

10. The compound according to claim 3 wherein X is methyl; and each of R$^1$ and R$^2$ is phenyl.

11. A pharmaceutically acceptable composition comprising a pharmaceutically acceptable carrier and a cyclooxygenase and/or 5-lipoxygenase inhibiting amount of a compound according to claim 1.

12. A method for treating inflammatory diseases in a mammal arising from biological mediators selected from prostaglandins and leukotrienes formed by cyclooxygenase and/or 5-lipoxygenase catalyzed reactions in a mammalian body which comprises administering to a mammal in need of such treatment a cyclooxygenase and/or 5-lipoxygenase inhibiting amount of a compound of formula

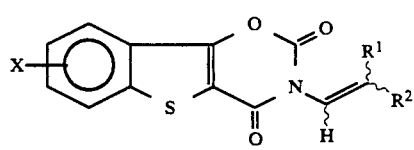 (II)

wherein X is hydrogen, trifluoromethyl, fluoro, chloro, lower alkyl, lower alkoxy, lower alkylthio, phenyl or 2,4-difluorophenyl;

each of R¹ and R² is hydrogen, phenyl, substituted phenyl wherein the substituent is chloro, fluoro, lower alkyl, lower alkoxy, lower alkylthio or hydroxy; furyl, thienyl, substituted thienyl wherein the substituent is lower alkyl, chloro or flouro; lower alkyl, chloro, lower alkoxycarbonyl; furyl or pyrryl.

* * * * *